United States Patent
Millauer et al.

[11] Patent Number: 5,808,163
[45] Date of Patent: *Sep. 15, 1998

[54] CHIRAL TERTIARY PHOSPHINES AND PROCESS FOR THEIR PREPARATION

[75] Inventors: Hans Millauer, Eschborn; Peter Brungs, Frankfurt, both of Germany

[73] Assignee: Aventis Research & Technologies GmbH & Co. KG, Frankfurt am Main, Germany

[*] Notice: The term of this patent shall not extend beyond the expiration date of Pat. No. 5,527,967.

[21] Appl. No.: 680,479

[22] Filed: Jul. 17, 1996

[30] Foreign Application Priority Data

Jul. 20, 1995 [DE] Germany ........................ 195 26 464.9

[51] Int. Cl.$^6$ ........................................................ C07F 9/50
[52] U.S. Cl. .................................. 568/17; 568/16; 568/15
[58] Field of Search .................................. 568/17, 16, 15

[56] References Cited

U.S. PATENT DOCUMENTS

| | | | |
|---|---|---|---|
| 4,306,082 | 12/1981 | Brunner | 568/17 |
| 5,288,912 | 2/1994 | Devon . | |
| 5,527,967 | 6/1996 | Millauer | 568/17 |

FOREIGN PATENT DOCUMENTS

| | | |
|---|---|---|
| 0268526 | 11/1987 | European Pat. Off. . |
| 0 684 248 A1 | 11/1995 | European Pat. Off. . |
| 4418346 | 11/1995 | Germany . |

OTHER PUBLICATIONS

Muller, E., *Houben–Weyl*, "Methoden der organischen Chemie", 4th Ed., vol. 12, Stuttgart, Georg Thieme Verlag, 1963, pp. 32–43 and 55–58.

Bentley, et al, *J. Chem. Soc., Perkin Trans.* 2:2531–1538, (1994).

*Journal of Organometallic Chemistry*, 95, vol. 495, pp. 103–111, Muller et al, Synthesis of monohydroxy –methyl– and –ethyl–phosphines PPh$_2$CHROH (1995).

*Primary Examiner*—Gary Geist
*Assistant Examiner*—Jean F. Vollano

[57] ABSTRACT

The invention relates to chiral tertiary alkyldiarylphosphines of the formula (I),

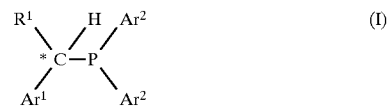

where:

$R^1$ is $(C_1-C_4)$alkyl, which can also be substituted by F, $CF_3$, $OCH_3$, $Ar^1$, $Ar^2$ are phenyl, naphthyl, anthracenyl, which can also bear one or more substituents selected from the group consisting of $(C_1-C_4)$alkyl, $(C_1-C_4)$alkoxy, $CF_3$, F, \* designates the chiral carbon atom which can have either an (R) or an (S) configuration, and also a process for preparing these compounds.

20 Claims, No Drawings

CHIRAL TERTIARY PHOSPHINES AND PROCESS FOR THEIR PREPARATION

DESCRIPTION

The invention relates to chiral tertiary alkyldiarylphosphines (I) and their preparation by nucleophilic substitution of chiral quaternary ammonium compounds (II) by salts of diarylphosphine anions (III).

The complexes of various heavy metal atoms with optically active, tertiary phosphines as ligands are used as catalysts in a wide variety of asymmetric syntheses (Brunner, Zettlmeier, Handbook of Enantioselective Catalysis Vol. I+II, VCH Verlagsgesellschaft mbH, Weinheim).

In view of the great variety of possible uses of such catalysts, there is a need for new chiral phosphine ligands, on the one hand to supplement and expand the range of their possible uses and on the other hand to make it possible to carry out certain reactions particularly favorably.

This object is achieved by chiral tertiary alkyldiarylphosphines of the formula (I),

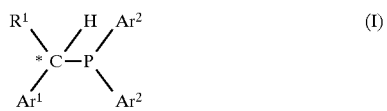

where:
- $R^1$ is $(C_1-C_4)$alkyl, which can also be substituted by F, $CF_3$, $OCH_3$,
- $Ar^1, Ar^2$ are phenyl, naphthyl, anthracenyl, which can also bear one or more substituents selected from the group consisting of $(C_1-C_4)$alkyl, $(C_1-C_4)$alkoxy, $CF_3$, F,
- * designates the chiral carbon atom which can have either an (R) or an (S) configuration.

Of interest here are the compounds where $Ar^1$, $Ar^2$ are phenyl or naphthyl which bear one or two substituents selected from the group consisting of $CF_3$, F, $OCH_3$, $CH_3$, and $R^1$ is an unsubstituted $(C_1-C_4)$alkyl radical.

The compounds in which $Ar^1$ and $Ar^2$ are unsubstituted phenyl or naphthyl and $R^1$ is a $CH_3$ group are naturally also important.

In principle, tertiary alkyldiarylphosphines can be prepared by two different methods. The most frequently used method is the reaction of a suitable organometallic compound such as a Grignard compound with diarylchlorophosphines ("Methoden der organischen Chemie", Houben-Weyl, 4th edition [1963], vol. XII/1, p. 32ff).

A disadvantage of this method is that the corresponding organometallic compounds cannot be obtained or obtained only with difficultly, particularly when certain additional substituents such as keto or ester groups are present. In addition, undesired coupling or ring closure reactions have often been observed in place of the intended formation of a C—P bond.

A second known method is to produce the metal salt of a diarylphosphine anion and react it with an alkyl halide. However, this method is not generally usable and gives satisfactory to good yields only with pure alkyl radicals or in the case of certain substituted alkyl radicals. In the case of araliphatic radicals, only moderate to poor yields (30% or 44% in the case of benzyl chloride) are achieved, as described in European Patent EP 0 268 526.

In addition, according to T. W. Bentley et al. (J. Chem. Soc., Perkin Trans. 2 (1994), 2531–8), benzylic halides react predominantly under $S_N1$ conditions, i.e. via the formation of carbocations. The synthesis of enantiomerically pure phosphines starting from benzyl halides which are chiral in the α position is therefore not possible.

These disadvantages apply to an even greater degree in the case of more reactive leaving groups such as tosylates or mesylates which, in the case of some aralkyl derivatives, decompose even at room temperature (T. W. Bentley et al., J. Chem. Soc., Perkin Trans. 2 (1994), 2531–8).

There was therefore a need for a process which avoids the disadvantages described and allows the compounds of the invention to be prepared in high yield and purity.

The preparation of aralkyl-substituted diarylphosphines by reaction of diarylphosphine aniones with quaternary aralkyl-substituted ammonium compounds has been described in the German Patent Application DE 44 18 346.

However, up to now only achiral tertiary phosphines have been produced using these methods. The synthesis of chiral aralkyldiarylphosphines (I) which can be used as optically active catalyst ligands in enantioselective syntheses has hitherto not been described by this method.

It has now surprisingly been found that the reaction of chiral benzylic quaternary ammonium compounds with salts of a diarylphosphine anion proceeds without racemization, i.e. the corresponding tertiary phosphines are obtained in enantiomerically pure form.

The invention accordingly also provides a process for preparing chiral aralkyldiarylphosphines of the formula (I), which comprises reacting chiral quaternary ammonium salts of the formula (II)

where $Ar^1$ and $R^1$ are as defined above, $R^2$, $R^3$ and $R^4$ are identical or different, straight-chain or branched $(C_1-C_{20})$ alkyl radicals and $X^-$ is an anion of an organic or inorganic acid,
with a salt of a diarylphosphine of the formula (III),

where $Ar^2$ is as defined above and $M^+$ is a metal cation.

The process is of great importance for preparing chiral tertiary phosphines because these compounds as ligands in homogeneously catalyzed processes expand the range of reactions which are already known and new reactions to be developed by the asymmetric variant and thus lead directly to optically active products. The synthesis of the chiral phosphines by the method presented here proceeds extremely efficiently in a simple manner and gives good yields.

The diarylphosphide of the formula (III) is either directly available commercially or can be obtained by metallization of a diarylphosphine, by reductive cleavage of a triarylphosphine or by reduction of a diarylphosphine of the formula (IV),

where $Ar^2$ is as defined above and Y is halogen, $(C_1-C_4)$ alkoxy, O-phenyl. The reduction can here be carried out in the presence of an ammonium compound of the formula (II), but it is also possible to carry out the reduction first and to add the ammonium compound subsequently.

The reduction of the diarylphosphines of the formula (IV) is preferably carried out electrochemically, but can also be carried out chemically, e.g. using metals, in particular alkali metals ("Methoden der organischen Chemie", Houben-Weyl, 4th edition, [1963], vol. XII/1, p. 56).

However, this procedure has the disadvantage compared with the electrochemical reduction that it would require use of techniques of organometallic synthesis which present safety difficulties. In the case of the electrochemical method, on the other hand, the reduction step is carried out in a very simple and readily controllable way starting from cheap, industrially available starting materials which are safe to handle.

Use is made of an undivided electrolysis cell which can be of any shape, for example a trough-shaped cell or a flow-through cell, which has at least one cathode and one anode.

The cathode comprises one of the customary metals, for example aluminum, magnesium, iron, nickel, chromium, titanium, copper, zinc, cadmium, silver, gold or platinum or alloys of these metals, preferably chromium-nickel steel, or carbon materials, for example graphite or vitreous carbon.

As anode, use is made of metals which are difficult to deposit cathodically under the electrolysis conditions, for example aluminum, calcium or preferably magnesium.

Suitable electrolytes are aprotic, dipolar solvents, for example acetonitrile, dimethylacetamide, N-methylpyrrolidone, tetrahydrofuran or preferably dimethylformamide.

If the quaternary ammonium compound is added only after the electrolysis, it is possible to add an additional, inert conductance salt which is soluble in the electrolyte, for example alkali or alkaline earth metal halides such as sodium bromide or preferably magnesium chloride.

The process of the invention is carried out at temperatures between about 0° C. and 80° C., preferably between 10° C. and 60° C.

The electrolysis is carried out at current densities between about 1 and 100 mA/cm², preferably between 5 and 50 mA/cm².

During the electrolysis, the electrolyte is advantageously moved relative to the electrodes by stirring or by flow. If the reaction is carried out with the quaternary ammonium compound present during the electrochemical reduction, the electrolyte can be stirred further for a certain time subsequent to the electrolysis to complete the reaction.

The process products are isolated in a manner known per se; for example by distilling off the solvent, dissolving the residue in a further water-immiscible solvent selected from the group consisting of hydrocarbons, halogenated hydrocarbons, ethers or ketones, extracting said solution with dilute mineral acids, evaporating the solvent and isolating the crude product obtained as residue by fractional distillation or crystallization.

The following example serves to illustrate the invention without restricting it to the example.

The ammonium compounds of the formula (II) can be prepared by generally known methods, e.g. by reacting an alkyl halide with an amine ("Methoden der organischen Chemie", Houben-Weyl, 4th edition [1963], vol. XI/2, p. 593 ff).

EXAMPLE

An undivided electrolysis cell is used. The cell comprises a cylindrical glass vessel (diameter: 40 mm, height 110 mm) with cooling jacket and a ground glass lid provided with 3 smaller ground openings. The anode used is a magnesium rod (diameter: 10 mm, length: 100 mm; immersion depth: about 45 mm), the cathode used is a rectangular mesh of chromium-nickel steel (60×50 mm), which is shaped into a cylinder and is arranged concentrically around the anode (the distance between the electrodes is about 2 mm). The electrodes are held in the lid of the cell by stiff wires of chromium-nickel steel which serve as power leads. The cell is also equipped with a thermometer, a gas inlet tube for nitrogen combined with a bubble counter. A further opening located in the cell wall is closed by means of a septum of silicone rubber. The electrolyte is stirred by means of a magnetic stirrer bar.

The dry cell is charged with 50 ml of dimethylformamide (max. 0.1% of water) and 400 mg of magnesium chloride. A dried stream of nitrogen is passed through the mixture for ½ hour while stirring, 6,49 g (0,029 mol) of chlorodiphenylphosphine is subsequently added through the septum and the electrolysis is started immediately thereafter with continued stirring and passing in of a gentle stream of nitrogen. The electric current is a constant 0,3 A, the temperature is 25° C. The cell potential is in the range from 0 to 1.5 volt. The amount of charge is 0.92 Ah. After the electrolysis is complete, 6,9 g (0,021 mol) of R-(1-phenylethyl) triethylammonium iodide are added and the reaction mixture is left stirring for 4 hours at 25° C.

The work-up is carried out under an atmosphere of N₂. The electrolyte is first evaporated on a rotary evaporator at 70° C./20 mbar, the residue obtained is taken up in 100 ml 2N hydrochloric acid and 70 ml of methylene chloride and stirred. The two phases are separated, the organic phase is washed once more with 100 ml of water and the solvent is distilled off. The residue is recrystallized from 15 ml of ethanol, filtered off and washed with 10 ml of ethanol. This gives 5 g (83% yield based on the ammonium compound used) of S-(1-phenylethyl)diphenylphosphine which, according to chiral HPLC on a Chiralcel OD column (eluant: n-hexane/2-propanol=95/5), is obtained in enantiomerically pure form.

Mp.: 108.5° C.
$[\alpha]_D = -265°$ (c = 1.7; $CH_2Cl_2$)

¹H-NMR: (300 MHz/CDCl₃): δ = 1.33(quartet, 3H, J = 7.5 Hz)
3.46(quintet, 1H, J = 7.5 Hz)
6.96–7.14(multiplet, 10H)
7.28–7.36(multiplet, 3H)
7.51–7.60(multiplet, 2H)
³¹P-NMR: (162 MHz/CDCl₃): δ = 3.45

What is claimed is:

1. A chiral tertiary alkyldiarylphosphine of the formula (I),

wherein:
R¹ is substituted or unsubstituted ($C_1$–$C_4$) alkyl, wherein the substituents are selected from the group consisting of: F, $CF_3$, and $OCH_3$;
Ar¹ and Ar² are each independently of one another substituted or unsubstituted phenyl, substituted or unsubstituted naphthyl, or substituted or unsubstituted anthracenyl, wherein the substituents are selected from the group consisting of ($C_1$–$C_4$)alkyl, ($C_1$–$C_4$)alkoxy, $CF_3$, and F, and

* designates the chiral carbon atom which can have either an (R) or an (S) configuration such that said tertiary alkyldiarylphosphine of formula I is in essentially enantiomerically pure form.

2. A compound as claimed in claim 1, wherein $Ar^1$, and $Ar^2$ are each independently of one another substituted or unsubstituted phenyl or substituted or unsubstituted naphthyl, wherein the substituted phenyl or substituted naphthyl may bear up to two substituents selected from the group consisting of $CF_3$, F, $CH_3$, and $OCH_3$, and $R^1$ is an unsubstituted $(C_1-C_4)$alkyl radical.

3. A compound as claimed in claim 1, wherein $Ar^1$ and $Ar^2$ are each independently of one another unsubstituted phenyl or naphthyl, and $R^1$ is a $CH_3$ group.

4. A process for preparing chiral aralkyldiarylphosphines of formula (I)

wherein:

$R^1$ is substituted or unsubstituted $(C_1-C_4)$ alkyl, wherein the substituents are selected from the group consisting of: F, $CF_3$, and $OCH_3$;

$Ar^1$ and $Ar^2$ are each independently of one another substituted or unsubstituted phenyl substituted or unsubstituted naphthyl, or substituted or unsubstituted anthracenyl, wherein the substituents are selected from the group consisting of $(C_1-C_4)$alkyl, $(C_1-C_4)$alkoxy, $CF_3$, and F, and

* designates the chiral carbon atom which can have either an (R) or an (S) configuration such that said tertiary alkyldiarylphosphine of formula I is in essentially enantiomerically pure form, which comprises a. reacting a chiral quaternary ammonium salt of the formula (II)

wherein:

$Ar^1$ and $R^1$ are as defined above, and $R^2$, $R^3$ and $R^4$ are identical or different, and are each a straight-chain or branched $(C_1-C_{20})$alkyl radical: and $X^-$ is an anion of an organic or inorganic acid, with a salt of a diarylphosphine of the formula (III),

where $Ar^2$ is defined in the same manner as $Ar^1$, defined above, and $M^+$ is a metal cation, in a reaction medium, and b. recovering an essentially enantiomerically pure form of said aralkyldiarylphosphine of the formula (I) from said reaction medium.

5. The process as claimed in claim 4, wherein the salt of the diarylphosphine of the formula (III) is prepared from a diarylphosphine of the formula (IV),

by electrochemical reduction, wherein Y is halogen, $(C_1-C_4)$alkoxy, or O-phenyl.

6. The process as claimed in claim 5, wherein the electrochemical reduction of formula (IV) is carried out in an undivided electrolysis cell having a cathode comprising a material selected from the group consisting of: aluminum, magnesium, iron, nickel, chromium, titanium, copper, zinc, cadmium, silver, gold, platinum, alloys of these metals and carbon materials, and an anion comprising a material selected from the group consisting of: aluminum, calcium and magnesium.

7. The process as claimed in claim 5, wherein the anode used is chromium-nickel steel and the cathode used is magnesium.

8. The process as claimed in claim 6, wherein the anode used is chromium-nickel steel and the cathode used is magnesium.

9. The process as claimed in claim 5, wherein electrolytes comprising aprotic, dipolar solvents are used in the electrochemical reduction.

10. The process as claimed in claim 9 wherein the aprotic, dipolar solvent is selected from the group consisting of: acetonitrile, dimethylacetamide, N-methylpyrrolidone, dimethylformamide, tetrahydrofuran, and dimethylformamide.

11. The process as claimed in claim 6, wherein electrolytes comprising aprotic, dipolar solvents are used in the electrochemical reduction.

12. The process as claimed in claim 11 wherein the aprotic, dipolar solvent is selected from the group consisting of: acetonitrile, dimethylacetamide, N-methylpyrrolidone, dimethylformamide, tetrahydrofuran, and dimethylformamide.

13. The process as claimed in claim 5, wherein the electrochemical reduction is carried out at current densities between about 1 and about 100 mA/cm$^2$.

14. The process as claimed in claim 5, wherein the electrochemical reduction is carried out at current densities between about 5 and about 50 mA/cm$^2$.

15. The process as claimed in claim 6, wherein the electrochemical reduction is carried out at current densities between about 1 and about 100 mA/cm$^2$.

16. The process as claimed in claim 6, wherein the electrochemical reduction is carried out at current densities between about 5 and about 50 mA/cm$^2$.

17. The process as claimed in claim 4, carried out at a reaction temperature between about 0° and about 80° C.

18. The process as claimed in claim 4, carried out at a reaction temperature between about 10° and about 60° C.

19. The process as claimed in claim 5, carried out at a reaction temperature between about 0° and about 80° C.

20. The process as claimed in claim 5, carried out at a reaction temperature between about 10° and about 60° C.

* * * * *